(12) United States Patent
Alam et al.

(10) Patent No.: US 8,586,602 B2
(45) Date of Patent: Nov. 19, 2013

(54) DERIVATIVES OF 7 ALKYNYL-1,8 NAPHTHYRIDONES, PREPARATION METHOD THEREOF AND USE OF SAME IN THERAPEUTICS

(75) Inventors: Antoine Alam, Villeneuve Tolosane (FR); Francoise Bono, Toulouse (FR); Oliver Duclos, Paris (FR); Gary McCort, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/486,414

(22) Filed: Jun. 1, 2012

(65) Prior Publication Data

US 2012/0238598 A1    Sep. 20, 2012

Related U.S. Application Data

(63) Continuation of application No. 12/631,130, filed on Dec. 4, 2009, now Pat. No. 8,263,614, which is a continuation of application No. PCT/FR2008/000794, filed on Jun. 11, 2008.

(30) Foreign Application Priority Data

Jun. 13, 2007 (FR) .................... 07 04193

(51) Int. Cl.
*A61K 31/44*    (2006.01)

(52) U.S. Cl.
USPC ........................................ 514/300

(58) Field of Classification Search
USPC ........................................ 514/300
See application file for complete search history.

(56) References Cited

U.S. PATENT DOCUMENTS

| | | |
|---|---|---|
| 2004/0147535 A1 | 7/2004 | Huth et al. |
| 2004/0254185 A1 | 12/2004 | Ernst et al. |
| 2010/0144757 A1 | 6/2010 | Alam et al. |

FOREIGN PATENT DOCUMENTS

| | | |
|---|---|---|
| EP | 0 978 516 A1 | 2/2000 |
| WO | 97/04775 | 2/1997 |
| WO | 02/094823 A1 | 11/2002 |
| WO | 2005/118587 A1 | 12/2005 |

OTHER PUBLICATIONS

Byzova et al., Blood, (Jun. 15, 2002) vol. 99, No. 12, pp. 4434-4442.*
U.S. Appl. No. 12/631,122, filed Dec. 4, 2009, Alam et al.
Boto et al., Organic Letters, (2004), vol. 6(21), pp. 3785-3788.
Ishikawa et al, Preparation of Carboxylic Acid Fluorides Using Hexafluoro-1,2- Epoxypropane, Chem. Lett., 1976 pp. 1407-1408.
Muakaiyama et al, A Convenient Method for the Preparation of Carboxylic Acid Fluorides, Chem. Lett., 1976 pp. 303-306.
Olah et al, Synthetic Methods and Reactions; IV. Fluorination of Carboxylic Acids with Cyanuric Fluoride, Synthesis, 1973 pp. 487-488.

* cited by examiner

*Primary Examiner* — Niloofar Rahmani
(74) *Attorney, Agent, or Firm* — Scully, Scott, Murphy & Presser, P.C.

(57) ABSTRACT

The disclosure relates to method of treating a disease in which VEGFR-3 is involved, comprising administering a therapeutically effective amount of a compound of the formula

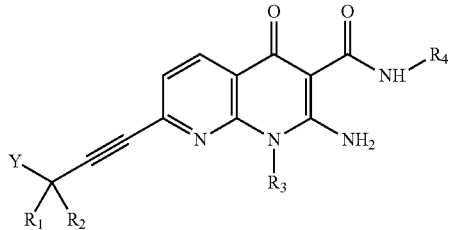

wherein $R_1$, $R_2$, $R_3$, and $R_4$ are as defined in the disclosure, to compositions containing them, to processes for preparing them, and to their use in therapeutics.

8 Claims, No Drawings

DERIVATIVES OF 7 ALKYNYL-1,8 NAPHTHYRIDONES, PREPARATION METHOD THEREOF AND USE OF SAME IN THERAPEUTICS

This application is a divisional of U.S. patent application Ser. No. 12/631,130 filed Dec. 4, 2009, which is a continuation of International Application No. PCT/FR2008/000794 filed Jun. 11, 2008, the entire contents of which are incorporated herein by reference The present invention relates to 7-alkynyl-1,8-naphthyridone derivatives, to their preparation and to their therapeutic application.

A subject matter of the present invention is compounds corresponding to the formula (I):

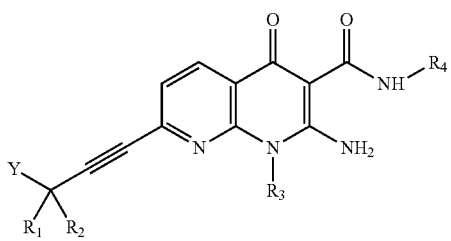

in which:

$R_1$ and $R_2$ represent, independently of one another:
- a hydrogen atom,
- a $C_1$-$C_7$ alkyl group optionally substituted by one or more alkoxy groups, $R_3$ represents a $C_1$-$C_7$ alkyl group,
$R_4$ represents a hydrogen atom or a $C_1$-$C_4$ alkyl group,
Y represents a $C_1$-$C_4$ alkoxy group or an —NRR' or —O(CH$_2$)$_n$—C(O)—NRR' group where R and R' are as defined below and n is an integer equal to 1 or 2,
R" represents a $C_1$-$C_4$ alkyl group, and
R and R' represent, independently of one another, a hydrogen atom, a —CO—($C_1$-$C_4$ alkyl) group or a —COOR" group, where R" is as defined above.

The compounds of formula (I) can comprise one or more asymmetric carbon atoms. They can therefore exist in the form of enantiomers or diastereoisomers. These enantiomers, diastereoisomers and their mixture, including their racemic mixture, come within the invention.

The compounds of formula (I) can exist in the form of bases or salified by acids or bases, in particular pharmaceutically acceptable acids or bases. Such addition salts come within the invention. These salts are advantageously prepared with pharmaceutically acceptable acids or bases but the salts of other acids or bases, for example of use in the purification or the isolation of the compounds of formula (I), also come within the invention.

The compounds according to the invention can also exist in the form of hydrates or solvates, namely in the form of combinations or associations with one or more molecules of water or with a solvent. Such hydrates and solvates also come within the invention.

In the context of the present invention and unless otherwise mentioned in the text:

an alkyl group is understood to mean a saturated, linear or branched, aliphatic group comprising from 1 to 7 carbon atoms (advantageously from 1 to 4 carbon atoms). Mention may be made, as examples, of the methyl, ethyl, propyl, isopropyl, butyl, isobutyl, tert-butyl, pentyl, hexyl or heptyl groups, and the like;

an alkoxy group is understood to mean an —O-alkyl group, where the alkyl group is as defined above;

a halogen atom is understood to mean a fluorine, a chlorine, a bromine or an iodine.

Mention may be made, among the compounds which are a subject matter of the invention, of a subgroup of compounds for which Y represents a $C_1$-$C_4$ alkoxy group.

Mention may be made, among the compounds which are a subject matter of the invention, of a second subgroup of compounds for which Y represents an —NRR' group where R and R' are as defined above.

Mention may be made, among the compounds which are subject matters of the invention, of a third subgroup of compounds for which Y represents an —O(CH$_2$)$_n$—C(O)—NRR' group where R and R' are as defined above and n is an integer equal to 1 or 2.

Mention may in particular be made, among the compounds which are subject matters of the invention, of the following compounds:

methyl {3-[7-amino-8-ethyl-6-(methylcarbamoyl)-5-oxo-5,8-dihydro-1,8-naphthyridin-2-yl]prop-2-yn-1-yl}carbamate 2-amino-7-(3-amino-3-methylbut-1-yn-1-yl)-1-ethyl-N-methyl-4-oxo-1,4-dihydro-1,8-naphthyridine-3-carboxamide hydrochloride (±)-2-amino-7-(3,4-dimethoxy-3-methylbut-1-yn-1-yl)-1-ethyl-N-methyl-4-oxo-1,4-dihydro-1,8-naphthyridine-3-carboxamide 2-amino-7-[3-(2-amino-2-oxoethoxy)-3-methylbut-1-yn-1-yl]-1-ethyl-N-methyl-4-oxo-1,4-dihydro-1,8-naphthyridine-3-carboxamide 2-amino-1-ethyl-7-(3-methoxyprop-1-yn-1-yl)-N-methyl-4-oxo-1,4-dihydro-1,8-naphthyridine-3-carboxamide.

In accordance with the invention, the compounds of formula (I) can be prepared according to the process presented in scheme 1.

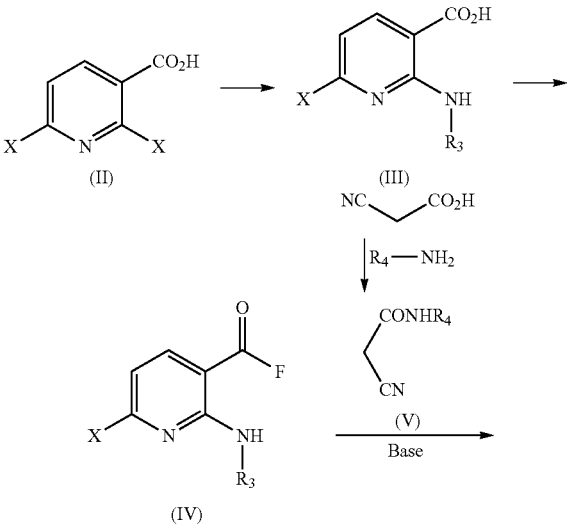

Scheme 1

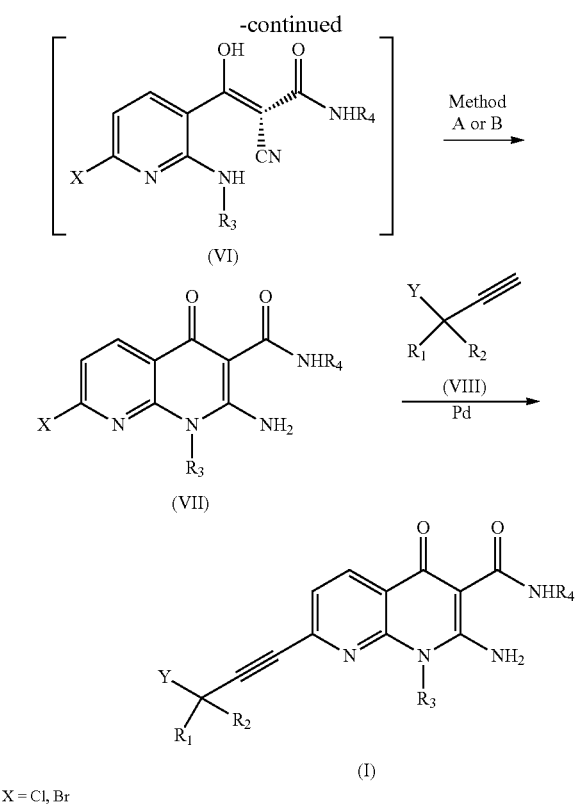

X = Cl, Br

According to scheme 1, a 2,6-dihalonicotinic acid of formula (II), where the X groups represent halogen atoms (preferably chlorine or bromine), which is either commercially available or prepared according to methods known to a person skilled in the art, is monosubstituted at the 2 position by an amine of formula $R_3$—$NH_2$ (where $R_3$ is as defined above in connection with the compounds of formula (I) which are subject matters of the invention), at a temperature of between 20° C. and 150° C., in a protic solvent, such as an alcohol or water, and optionally in a sealed tube. A 2-aminonicotinic derivative of formula (III) is obtained, which derivative is converted to the acid fluoride of formula (IV) by the action of cyanuric fluoride at ambient temperature, in the presence of a base, such as triethylamine or pyridine, and in an inert solvent, such as dichloromethane, as described by G. Olah et al. in *Synthesis* (1973), 487, or by other methods known to a person skilled in the art, such as those described by Mukaiyama and Tanaka in *Chem. Lett.* (1976), 303, or by Ishikawa and Sasaki in *Chem. Lett.* (1976), 1407. The acyl fluorides of formula (IV), which are highly reactive but stable, are subsequently reacted with an N-substituted cyanoacetamide of formula (V) in the presence of a strong base, such as sodium hydride, in a polar aprotic solvent, such as dimethylformamide.

When two equivalents of sodium hydride are employed in the stage of condensation of the derivative (IV) with a derivative (V) and then a third equivalent of NaH is introduced after stirring at ambient temperature for between 10 and 16 hours, the deprotonated compound (VI) formed cyclizes in situ at the same temperature with good yields to directly provide the aminopyridino[2,3-b]pyridone of formula (VII) (method B).

The N-alkylcyanoacetamides of formula (V) are prepared by reacting cyanoacetic acid with an alkyl chloroformate (such as ethyl or isobutyl chloroformate) in the presence of a base, such as triethylamine, at a temperature of less than or equal to 0° C., and then the mixed anhydride intermediate formed is reacted with an excess of amine of formula $R_4$—$NH_2$ (where $R_4$ is as defined above in connection with the compounds for formula (I) which are subject matters of the invention).

In order to obtain a pyridino[2,3-b]pyridinone of formula (I) which is a subject matter of the present invention, the halogenated intermediate of formula (VII) is coupled, according to the methods known to a person skilled in the art, with an appropriate derivative of propargyl alcohol $R_1R_2CH(Y)CCH$ of formula (VIII), where $R_1$, $R_2$ and Y are as defined for the compounds of formula (I). For example, the intermediate (VII) is involved in a Sonogashira coupling reaction with the appropriate alkyne of formula (VIII) in the presence of $PdCl_2(PPh_3)_2$, copper iodide, triethylamine and dimethylformamide at a temperature of between 80° C. and 120° C. This reaction can be carried out in a sealed tube and under microwave radiation.

If necessary, during the reaction stages presented in scheme 1, certain reactive functional groups situated on the Y, $R_1$, $R_2$ and $R_3$ groups can be temporarily protected by protective groups known to a person skilled in the art, such as described in "Protective Groups in Organic Synthesis", Green et al., 2nd edition (John Wiley & Sons Inc., New York).

In scheme 1, the starting compounds and their reactants, when their method of preparation is not described, are available commercially or described in the literature or else can be prepared according to methods which are described therein or which are known to a person skilled in the art.

Another subject matter of the invention, according to another of its aspects, is the compounds of formula (VII) defined in scheme 1. These compounds are of use as intermediates in the synthesis of the compounds of formula (I).

The following examples illustrate the preparation of some compounds in accordance with the invention. These examples are not limiting and serve only to illustrate the present invention. The numbers of the compounds given in the examples refer to those given in the table below, in which the chemical structures and the physical properties of a few compounds according to the invention are illustrated.

EXAMPLE 1

(±)-2-Amino-7-(3,4-dimethoxy-3-methylbut-1-yn-1-yl)-1-ethyl-N-methyl-4-oxo-1,4-dihydro-1,8-naphthyridine-3-carboxamide (compound No. 1)

1.1: 2-(Ethylamino)-6-chloronicotinic acid

A solution of 18.0 g (84.4 mmol) of 2,6-dichloronicotinic acid in 180 ml of a 70% solution of ethylamine in water is stirred at ambient temperature for 72 hours. The excess amine is then evaporated under reduced pressure and then a 10% aqueous acetic acid solution is added until the product precipitates. The beige solid is filtered off, rinsed with cold water and dried in an oven. 10.5 g of the expected product are obtained. Melting point: 158-160° C. Yield=62%.

1.2: 2-(Ethylamino)-6-chloronicotinic acid fluoride 2 ml (24.8 mmol) of pyridine and 4.2 ml (49.8 mmol) of 2,4,6-trifluorotriazine are added to a suspension of 5.0 g (24.8 mmol) of 2-(ethylamino)-6-chloronicotinic acid in 125 ml of dichloromethane. The mixture is stirred at ambient temperature for 3 hours and then filtered. The solid is rinsed with 50 ml of dichloromethane and the filtrate is washed twice with 60 ml of ice-cold water. The organic phase is dried over Na$_2$SO$_4$ and the solvent is evaporated under reduced pressure. 5.01 g of product are obtained in the form of an orange oil. Yield=99%.

1.3: N-Methylcyanoacetamide 12.28 ml (128.44 mmol) of ethyl chloroformate are added dropwise to a solution, cooled to −30° C., of 10.0 g (116.38 mmol) of 99% cyanoacetic acid and 16.3 ml (116.9 mmol) of triethylamine in 100 ml of anhydrous THF and then the mixture is stirred at −30° C. for one and a half hours. 300 ml of methanol saturated with gaseous methylamine are subsequently added dropwise and then the mixture is stirred at ambient temperature overnight. The solvents are evaporated under reduced pressure and the product is purified by filtration through silica gel, the elution being carried out with a dichloromethane:methanol (95:5) mixture. 10.0 g of product are obtained in the form of a beige solid. Melting point=99° C. Yield=87%.

Method A (Parts 1.4 and 1.5 Below)

1.4: 3-[6-Chloro-2-(ethylamino)-3-pyridinyl]-2-cyano-3-hydroxy-N-methyl-2-propenamide 3.98 g (100 mmol) of 60% sodium hydride in mineral oil are added in small amounts to a solution, cooled to 0-5° C., of 9.80 g (100 mmol) of N-methylcyanoacetamide in 100 ml of anhydrous dimethylformamide. After hydrogen has finished being given off, the mixture is stirred at ambient temperature for 10 minutes and is then again cooled to 0-5° C. A solution of 10.09 g (49.8 mmol) of 2-(aminoethyl)-6-chloronicotinic acid fluoride in 60 ml of dimethylformamide is then added and the medium is stirred at ambient temperature overnight. 2.85 ml (49.8 mmol) of acetic acid are added and the volatile materials are evaporated under reduced pressure. The residue is taken up in water and the product is extracted twice with a dichloromethane:methanol (95:5) mixture and then once with an ethyl acetate:THF (2:1) mixture. The combined organic phases are dried over MgSO$_4$ and then the solvents are evaporated under reduced pressure. 19.0 g of product are obtained, which product is used as is in the following stage.

1.5: 2-Amino-7-chloro-1-ethyl-N-methyl-4-oxo-1,4-dihydro-1,8-naphthyridine-3-carboxamide A solution of 19.0 g of the crude product obtained on conclusion of stage 7.4 (49.8 mmol) in 600 ml of n-butanol is heated at 110° C. for 48 hours. The solvent is evaporated under reduced pressure and the solid obtained is triturated from methanol. The solid is subsequently filtered off and dried in an oven. 7.9 g of the expected product are obtained in the form of a pale yellow solid. Melting point: 283-286° C. Yield=57%.

Method B (Part 1.6 Below Instead of 1.4 and 1.5)

1.6: 2-Amino-7-chloro-1-ethyl-N-methyl-4-oxo-1,4-dihydro-1,8-naphthyridine-3-carboxamide 0.394 g (9.95 mmol) of 60% sodium hydride in mineral oil is added in small amounts to a solution, cooled to 0-5° C., of 0.483 g (4.93 mmol) of N-methylcyanoacetamide in 7 ml of anhydrous dimethylformamide. Stirring is continued at this temperature for 10 minutes and then a solution of 1.0 g (4.93 mmol) of 2-(aminoethyl)-6-chloronicotinic acid fluoride in 5 ml of dimethylformamide is added. The medium is stirred overnight at ambient temperature and then a further 0.197 g (4.93 mmol) of 60% sodium hydride is added in small amounts. Stirring is continued at this temperature for 10 minutes and then 0.56 ml (9.78 mmol) of acetic acid is added. 60 ml of water are subsequently added and the solid is filtered off, rinsed with water and then dried in an oven. 1.30 g of the expected product are obtained. Melting point: 283-284° C. MH$^+$=281. Yield=94%.

$^1$H NMR (d$_6$-DMSO, 400 MHz, δ in ppm): δ 11.75 (s, <1H, very broad); 11.00 (q, 1H, broad); 8.45 (d, 1H); 8.10 (s, 1H, broad); 7.40 (d, 1H); 4.40 (q, 2H); 2.80 (d, 3H); 1.25 (t, 3H).

1.7: Preparation of (±)-3,4-dimethoxy-3-methylbut-1-yne 1400 ml (0.7 mol) of a 0.5M commercial solution of ethynylmagnesium chloride (or bromide) in tetrahydrofuran are run into a three-necked flask under argon. Cooling is carried out to 2° C. with an ice bath and the solution of 30 g (0.327 mol) of methoxyacetone in 600 ml of tetrahydrofuran is slowly added (exothermic). Stirring is carried out at 2° C. for 1 hour and then the reaction mixture is poured onto an ice/saturated aqueous NH$_4$Cl mixture. Extraction is carried out with ether and then the organic phases are combined, dried with sodium sulfate, filtered and concentrated under limited vacuum. Finally, (±)-1-methoxy-2-methyl-3-butyn-2-ol is obtained in the form of a brown oil weighing 38 g (quantitative crude yield) which is used without subsequent purification in the following stage.

17.5 ml of the 1.0M solution of potassium tert-butoxide in tetrahydrofuran (Aldrich; 17.52 mmol) are added to a solution, cooled with an ice bath, of 2 g of (±)-1-methoxy-2-methyl-3-butyn-2-ol (17.52 mmol) in 6 ml of tetrahydrofuran. Stirring is carried out at ambient temperature for 30 minutes and then 0.55 ml of methyl iodide (35.04 mmol) is added. The reaction mixture is stirred at ambient temperature for 3 hours and then is diluted with ether and water. After separation by settling, the organic phase is washed with water, dried over sodium sulfate, filtered and concentrated under limited vacuum. 2.4 g of the expected product are obtained in the form of a yellow oil comprising residual ether and residual tetrahydrofuran. The (±)-3,4-dimethoxy-3-methylbut-1-yne obtained is used in the following stage without subsequent purification.

1.8: (±)-2-Amino-7-(3,4-dimethoxy-3-methylbut-1-yn-1-yl)-1-ethyl-N-methyl-4-oxo-1,4-dihydro-1,8-naphthyridine-3-carboxamide A suspension of 1.5 g (5.34 mmol) of 2-amino-7-chloro-1-ethyl-N-methyl-4-oxo-1,4-dihydro-1,8-naphthyridine-3-carboxamide in 30 ml of a DMF/Et$_3$N (v/v; 2/1) mixture is placed in an 80 ml microwave tube. Argon is sparged into this suspension for 10 minutes and then 1.37 g of (±)-3,4-dimethoxy-3-methylbut-1-yne (10.69 mmol), 0.101 g of CuI (0.53 mmol) and 0.187 g of bis(triphenylphosphine)palladium(II)dichloride (0.27 mmol) are successively added.

The sealed tube is placed in the microwave oven (CEM device, Discover model) and the mixture is heated under pressure at 80° C. for 45 minutes (P=100 W) and then cooled and evaporated to dryness. The residue is taken up in ethyl acetate and water. The aqueous phase is extracted with ethyl acetate (3 times) and then the organic phases are combined, dried over sodium sulfate, filtered and concentrated under vacuum.

The residue obtained is purified by chromatography on a silica column (solid deposit; elution with a dichloromethane:methanol 100:0 to 98:2 gradient). 1.37 g of the expected product are obtained in the form of a pale gray powder.

Melting point=185-187° C. MH+=373. Yield=69%.

$^1$H NMR (d$_6$-DMSO, 400 MHz, δ in ppm): δ 11.75 (s, <1H, very broad); 11.00 (q, 1H, broad); 8.45 (d, 1H); 8.00 (s, 1H, broad); 7.4 (d, 1H); 5.8 (s, 1H); 4.4 (q, 2H); 3.5-3.3 (m+s, 5H); 2.8 (d, 3H); 1.45 (s, 3H); 1.2 (t, 3H).

EXAMPLE 2

Methyl {3-[7-amino-8-ethyl-6-(methylcarbamoyl)-5-oxo-5,8-dihydro-1,8-naphthyridin-2-yl]prop-2-yn-1-yl}carbamate (compound No. 2)

2.1: Methyl (prop-2-yn-1-yl)carbamate

A solution of 1.3 ml of propargylamine (18.95 mmol, Aldrich) in 19 ml of dioxane is cooled to 0° C. and then 19 ml of a saturated aqueous NaHCO$_3$ solution are added. Stirring is carried out at 0° C. for 30 minutes and then 1.83 ml of methyl chloroformate (23.68 mmol) are added. The reaction mixture is stirred overnight while allowing the temperature to gradually return to ambient temperature. The mixture is extracted 4 times with ether and then the organic phases are combined, dried over sodium sulfate, filtered and concentrated under vacuum. 1.93 g of the expected product are obtained in the form of a yellow oil (yield=90%) which is used without subsequent purification.

2.2: Methyl {3-[7-amino-8-ethyl-6-(methylcarbamoyl)-5-oxo-5,8-dihydro-1,8-naphthyridin-2-yl]prop-2-yn-1-yl}carbamate A suspension of 0.8 g (2.85 mmol) of 2-amino-7-chloro-1-ethyl-N-methyl-4-oxo-1,4-dihydro-1,8-naphthyridine-3-carboxamide in 22 ml of a DMF/Et$_3$N (v/v; 2.2/1) mixture is placed in a 10 ml microwave tube. Argon is sparged into this suspension for 10 minutes and then 0.98 g of methyl (prop-2-yn-1-yl)carbamate (8.66 mmol), 0.076 g of CuI (0.40 mmol) and 0.139 g of bis(triphenylphosphine)palladium(II) dichloride (0.20 mmol) are successively added.

The sealed tube is placed in the microwave oven (CEM device, Discover model) and the mixture is heated under pressure at 90° C. for 15 minutes (P=50 W). After returning to ambient temperature, the mixture is evaporated to dryness and then the residue is taken up in ethyl acetate. The organic phase is washed successively with saturated aqueous NaHCO$_3$ and then with saturated aqueous NaCl. The insoluble material is separated and subsequently triturated from methanol, tetrahydrofuran and ether. 0.284 g of a solid is obtained and is purified by chromatography on a silica column (solid deposit after dissolving in a tetrahydrofuran/methanol mixture and then elution with a dichloromethane:methanol 100:0 to 98:2 gradient). 0.095 g of the expected product is obtained in the form of a white solid.

Melting point=255° C. MH+=357. Yield=9.3%.

$^1$H NMR (d$_6$-DMSO, 400 MHz, δ in ppm): δ 11.70 (s, <1H, very broad); 11.00 (q, 1H, broad); 8.40 (d, 1H); 8.00 (s, 1H, broad); 7.75 (t, 1H, broad); 7.40 (d, 1H); 4.40 (q, 2H); 4.10 (d, 2H); 3.55 (s, 3H); 2.80 (d, 3H); 1.20 (t, 3H).

EXAMPLE 3

2-Amino-7-(3-amino-3-methylbut-1-yn-1-yl)-1-ethyl-N-methyl-4-oxo-1,4-dihydro-1,8-naphthyridine-3-carboxamide hydrochloride (compound No. 4)

A suspension of 0.84 g (3.0 mmol) of 2-amino-7-chloro-1-ethyl-N-methyl-4-oxo-1,4-dihydro-1,8-naphthyridine-3-carboxamide in 20 ml of a DMF/Et$_3$N (v/v; 7/3) mixture is placed in a 10 ml microwave tube. Nitrogen is sparged into this suspension for 10 minutes and then 0.50 g of 2-methylbut-3-yn-2-amine (6.0 mmol), 0.089 g of CuI (0.47 mmol) and 0.149 g of bis(triphenylphosphine)palladium(II)dichloride (0.21 mmol) are successively added.

The sealed tube is placed in the microwave oven (CEM device, Discover model) and the mixture is heated under pressure at 90° C. for 15 minutes (P=50 W) and then at 100° C. for 25 minutes. After returning to ambient temperature, the mixture is evaporated to dryness and then the residue is taken up in ethyl acetate. The organic phase is washed successively with saturated aqueous NaHCO$_3$ and then with saturated aqueous NaCl, dried over sodium sulfate, filtered and concentrated under vacuum. The oily residue obtained is purified by chromatography on a silica column (elution with a dichloromethane:methanol 100:0 to 97:3 gradient). 0.151 g (0.46 mmol) of the expected product is obtained. This product is dissolved in 3 ml of ethyl acetate and then 0.13 ml (0.52 mmol) of a 4N solution of hydrochloric acid in dioxane is added. After filtering and drying in the oven under vacuum, 0.134 mg of expected product is obtained in the form of a yellow solid.

Melting point=293° C. MH+=310. Yield=12%.

$^1$H NMR (d$_6$-DMSO, 400 MHz, δ in ppm): δ 11.75 (s, <1H, very broad); 11.00 (q, 1H, broad); 8.40 (d, 1H); 8.10 (s, <1H, broad); 7.45 (d, 1H); 4.40 (q, 2H); 3.50 (dd, 2H); 3.35 (s, 6H); 2.85 (d, 3H); 1.45 (s, 3H); 1.20 (t, 3H).

EXAMPLE 4

2-Amino-7-[3-(2-amino-2-oxoethoxy)-3-methylbut-1-yn-1-yl]-1-ethyl-N-methyl-4-oxo-1,4-dihydro-1,8-naphthyridine-3-carboxamide (compound No. 6)

4.1: Ethyl [(1,1-dimethylprop-2-yn-1-yl)oxy]acetate

A solution of 0.87 g (10.32 mmol) of 2-methylbut-3-yn-2-ol in 20 ml of anhydrous THF is cooled to 0-5° C. with an ice bath and then 10.32 ml (10.32 mmol) of 1.0M potassium t-butoxide in THF (Aldrich) are added. Stirring is carried out under cold conditions for 10 minutes and then 1.89 g (11.35 mmol) of ethyl bromoacetate are added. The reaction mixture is stirred at ambient temperature for 45 minutes and then 0.1 N aqueous HCl and ether are added. The organic phase is dried over sodium sulfate, filtered and concentrated under vacuum. 1.45 g of the expected product are obtained in the form of a yellow oil which is used without subsequent purification. Yield=83%.

4.2: Ethyl ({3-[7-amino-8-ethyl-6-(methylcarbamoyl)-5-oxo-5,8-dihydro-1,8-naphthyridin-2-yl]-1,1-dimethylprop-2-yn-1-yl}oxy) acetate 1.15 g (4.10 mmol) of 2-amino-7-chloro-1-ethyl-N-methyl-4-oxo-1,4-dihydro-1,8-naphthyridine-3-carboxamide and 1.39 g (8.19 mmol) of ethyl [(1,1-dimethylprop-2-yn-1-yl)oxy]acetate are placed in a mixture of 10 ml of dimethylformamide and 10 ml of triethylamine. Argon is sparged into the reaction mixture for 15 minutes and then 0.031 g (0.16 mmol) of CuI and 0.144 g (0.20 mmol) of bis(triphenylphosphine)palladium(II)dichloride are successively added. The reaction mixture is heated at 90° C. for 15 hours. After returning to ambient temperature, the reaction mixture is poured onto a water/ice mixture. After separating them by settling, the black gum obtained is dissolved in ethyl acetate and then washed with water. The organic phase is dried over sodium sulfate, filtered and concentrated under vacuum. 1.4 g of a brown oil are obtained, which oil is purified by chromatography on silica (elution with a cyclohexane/ethyl acetate 30:70 to 20:80 gradient) to give 0.72 g of the expected product in the form of a yellow solid.

Yield=41%.

4.3: 2-Amino-7-[3-(2-amino-2-oxoethoxy)-3-methylbut-1-yn-1-yl]-1-ethyl-N-methyl-4-oxo-1,4-dihydro-1,8-naphthyridine-3-carboxamide 0.30 g (0.72 mmol) of ethyl ({3-[7-amino-8-ethyl-6-(methylcarbamoyl)-5-oxo-5,8-dihydro-1,8-naphthyridin-2-yl]-1,1-dimethylprop-2-yn-1-yl}oxy) acetate is placed in 30 ml of methanol in a 50 ml sealed tube. The solution is cooled with an ice bath and gaseous ammonia is sparged in to saturation. Heating is carried out at 80° C. for 8 hours and then the mixture is evaporated to dryness. The residue obtained is purified by chromatography on a silica column (solid deposit after dissolving in a tetrahydrofuran/methanol mixture and then elution with a dichloromethane:methanol 100:0 to 95:5 gradient) to give 0.18 g of the expected product in the form of a white solid Melting point=204° C. MH$^+$=386. Yield=64%.

$^1$H NMR (d$_6$-DMSO, 400 MHz, δ in ppm): δ 11.85 (s, <1H, very broad); 11.00 (q, 1H, broad); 8.45 (d, 1H); 7.45 (d, 1H); 7.20 (d, <2H, broad); 4.40 (q, 2H); 3.95 (s, 2H); 2.80 (d, 3H); 1.60 (s, 6H); 1.20 (t, 3H).

The chemical structures and the physical properties of a few compounds of formula (I) according to the invention are illustrated in the following table. In this table:

Me and Et respectively represent methyl and ethyl groups,
  in the "salt" column, "-" represents a compound in the form of the free base, while "HCl" represents a compound in the form of the hydrochloride,
  the M.p. column indicates the melting point, in ° C., of the compound, and
  in the LC/MS column, the high performance liquid chromatography analytical method used (A or B) and described in detail below, the retention time of the compound, expressed in minutes, and the MH$^+$ peak identified by mass spectrometry are successively indicated.

Method A:
Column: Gemini, 50×3 mm, 3 μm
Solvent A: H$_2$O+0.1% HCO$_2$H; solvent B: ACN+0.1% HCO$_2$H; flow rate=1 ml/min
Gradient: 95/5 (0 min) to 0/100 (5.5 min) to 0/100 (7.5 min)
Detection: 220 nM
Ionization: ESI+

Method B:
Column: Kromasil, 50×2.1 mm, 3.5 μm
Solvent A: CH$_3$CO$_2$NH$_4$ 5 mM; solvent B: ACN; flow rate=0.5 ml/min
Gradient: 100/0 (0 min) to 0/100 (13 min) to 0/100 (16 min)
Detection: 220 nM
Ionization: ESI+
  in the chirality column "/" represents an achiral compound and (±) represents a compound in the form of the racemic mixture.

TABLE

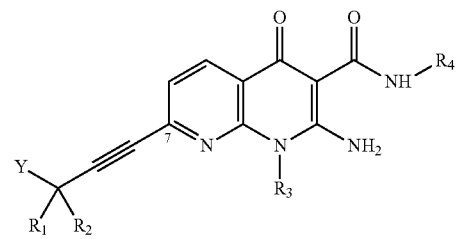

(I)

| No. | R$_1$ | R$_2$ | R$_3$ | R$_4$ | Y | Salt | LC/MS | M.p. | Chirality |
|---|---|---|---|---|---|---|---|---|---|
| 1 | Me | (R$_1$ and R$_2$ joined to CH-OMe group) | Et | Me | OMe | — | B 6.16 373 | 185-187 | (±) |
| 2 | H | H | Et | Me | —NH—C(=O)—O—Me | — | B 3.48 358 | 250 | / |
| 3 | H | H | Et | Me | —NH—C(=O)—Me | — | C 4.94 342 | 239 | / |

TABLE-continued

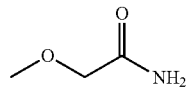

(I)

| No. | $R_1$ | $R_2$ | $R_3$ | $R_4$ | Y | Salt | LC/MS | M.p. | Chirality |
|-----|-------|-------|-------|-------|---|------|-------|------|-----------|
| 4 | Me | Me | Et | Me | $NH_2$ | HCl | B 4.08 327 | 293 | / |
| 5 | H | H | Et | Me | OMe | — | C 6.8 315 | 233 | / |
| 6 | Me | Me | Et | Me | ![OCH2C(O)NH2 group] | — | B 3.83 386 | 204 | / |

The compounds according to the invention have formed the subject of pharmacological assays which make it possible to determine their inhibitory effect on the VEGFR-3 enzyme. Measurement of the Tyrosine Kinase Activity of VEGFR-3 by ELISA The enzymatic activity of VEGFR-3 is evaluated on an ELISA assay by measuring the intensity of phosphorylation of the substrate poly Glu-Tyr. The effect of the products is quantified by the concentration which decreases the total activity of the enzyme by 50% ($IC_{50}$). For the determination of the $IC_{50}$ values, the product is diluted in DMSO with a concentration range which extends from 3 to 1000 nM. The day before the manipulation, 125 µl of the poly Glu-Tyr substrate (250 µg/ml in 1×PBS without $Ca^{2+}$ or $Mg^{2+}$ or sodium bicarbonate) are deposited in each well of an ELISA plate (for example, an ELISA plate of the SIGMA Protein Tyrosine Kinase Assay kit, Ref. PTK-101). The plate is subsequently covered with an adhesive film and incubated overnight at 37° C. The following day, the wells are emptied by turning the plate over, washed by adding 300 µl of buffer solution (PBS+0.05% Tween 20) and dried by further incubation of the plate for 2 h at 37° C. A 90 µl reaction mixture is deposited onto each well. This mixture comprises the 1× kinase buffer to which 30 µM of ATP and the inhibitor at the desired concentration have been added. Subsequently, 20 µl of VEGFR-3-TK (Cell Signaling, Ref. 7790), diluted beforehand in the kinase buffer without ATP, are added (with the exception of the negative control wells, where 20 µl of buffer without enzyme are added). The plates are subsequently incubated for 30 min at ambient temperature with gentle agitation. After 3 rinses with the buffer solution (300 µl/well per wash), 100 µl of anti-phosphotyrosine—HRP antibody (1/30 000) are added to each well and the plates are again incubated for 30 min at ambient temperature with gentle agitation. After 3 washes in buffer solution (300 µl/well per wash), the phosphorylation of the substrate is revealed by adding 100 µl per well of OPD substrate, 1 OPD tablet and 1 urea tablet in 20 ml of water (extemporaneous preparation in the dark). After incubation for 7 minutes at ambient temperature and in the dark, the reaction is stopped by adding 100 µl of 1.25 M (2.5N) $H_2SO_4$ per well, and the absorbance is read at 492 nm.

The total activity is evaluated by the difference in optical density obtained on samples incubated in the presence (stimulated) and in the absence (non-stimulated) of VEGFR-3.

The compounds in accordance with the invention exhibit $IC_{50}$ values of less than 10 µM, for the most part of less than 1 µM. By way of examples, compounds Nos 4 and 5 of the table exhibit $IC_{50}$ values of 451 nM and 343 nM respectively.

It is thus apparent that the compounds according to the invention have an inhibitory activity on the VEGFR-3 enzyme; they can thus be used in the preparation of medicaments, in particular of medicaments which are VEGFR-3 inhibitors.

Thus, according to another of its aspects, a subject matter of the invention is medicaments which comprise a compound of formula (I), or an addition salt of the latter with a pharmaceutically acceptable acid or base, or even a hydrate or a solvate, and also an enantiomer or a diastereoisomer, including their mixture, of the compound of formula (I).

Another aspect of the invention comprises a combination of at least one compound according to the invention and at least one chemotherapy agent.

Specifically, the compounds of the present invention can be used, alone or as a mixture, with at least one chemotherapy agent which can be chosen from:
alkylating agents,
intercalating agents,
antimicrotubule agents,
antimitotic agents,
antimetabolites,
antiproliferative agents,
antibiotics,
immunomodulatory agents,
anti-inflammatories,
kinase inhibitors,
antiangiogenic agents,
antivascular agents,
estrogenic and androgenic hormones,
and the prodrugs of the abovementioned agents or derivatives.

It is also possible to combine the compounds according to the invention with a radiation treatment.

The combinations of the compounds of the invention with the chemotherapy agents mentioned above and/or the radiation are another subject matter of the present invention.

The chemotherapy agents mentioned above and/or the radiation can be administered simultaneously, separately or sequentially. The treatment will be adjusted by the practitioner according to the patient to be treated.

These medicaments are used therapeutically, in particular in the treatment and prevention:
- of cancers and metastases thereof, such as: glioblastomas, multiple myelomas, myelodysplasic syndromes, Kaposi's sarcomas, solid tumors, lymphomas, melanomas, breast cancers, colorectal cancers, lung cancers, including non-small-cell cancers, pancreatic cancers, prostate cancers, kidney cancers, head and neck cancers, liver cancers, ovarian cancers, cancers of the respiratory tract and chest, tumor angiogeneses or other tumors expressing VEGFR-3 or involving a process of angiogenesis or of lymphangiogenesis,
- non-oncological proliferative diseases and pathological angiogenesis linked to VEGFR-3, such as: arthroses, restenoses, psoriasis, hemangiomas, glaucomas, glomerulonephritis, diabetic nephropathies, nephrosclerosis, thrombotic microangiopathic syndromes, liver cirrhosis, atherosclerosis, organ transplant rejection, or eye diseases involving a process of angiogenesis or of lymphangiogenesis, such as diabetic retinopathy or macular degeneration,
- or also in the treatment and prevention of inflammation (chronic or non-chronic), of infection by microorganisms and of autoimmune diseases, such as rheumatoid arthritis,
- or also in the treatment of rare diseases, such as lymphangioleiomyomatosis.

According to another of its aspects, the present invention relates to pharmaceutical compositions comprising, as active principle, a compound according to the invention. These pharmaceutical compositions comprise an effective dose of at least one compound according to the invention, or a pharmaceutically acceptable salt, a hydrate or a solvate of said compound, and at least one pharmaceutically acceptable excipient.

Said excipients are chosen, according to the pharmaceutical form and the method of administration desired, from the usual excipients known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its optional salt, solvate or hydrate, can be administered in unit administration form, as a mixture with conventional pharmaceutical excipients, to animals and human beings for the treatment or prevention of the above disorders or diseases.

The appropriate unit administration forms comprise oral forms, such as tablets, soft or hard gelatin capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. The compounds according to the invention can be used, for topical application, in creams, gels, ointments or lotions.

By way of example, a unit administration form of a compound according to the invention in the tablet form can comprise the following components:

| | |
|---|---|
| Compound according to the invention | 50.0 mg |
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

The present invention, according to another of its aspects, also relates to a method for the treatment of the pathologies indicated above which comprises the administration, to a patient, of an effective dose of a compound according to the invention or one of its pharmaceutically acceptable salts or its hydrates or its solvates.

What is claimed is:

1. A method treating a disease selected from the group consisting of restenosis, nephrosclerosis, and liver cirrhosis, comprising administering to a patient in need thereof an effective dose of a compound of formula (I):

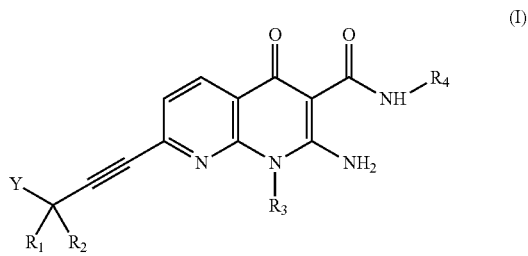

wherein:
$R_1$ and $R_2$ represent, independently of one another:
  a hydrogen atom, or
  a $C_1$-$C_7$ alkyl group optionally substituted by one or more alkoxy groups;
$R_3$ represents a $C_1$-$C_7$ alkyl group;
$R_4$ represents a hydrogen atom or a $C_1$-$C_4$ alkyl group;
Y represents a $C_1$-$C_4$ alkoxy group or an —NRR' or —O(CH$_2$)$_n$—C(O)—NRR' group where R and R' are as defined below and n is an integer equal to 1 or 2;
R" represents a $C_1$-$C_4$ alkyl group; and
R and R' represent, independently of one another, a hydrogen atom, a —CO—($C_1$-$C_4$ alkyl) group or a —COOR" group, where R" is as defined above;
  or an acid addition salt thereof, or an enantiomer or diastereoisomer thereof, or a mixture thereof.

2. The method according to claim 1 wherein the disease is restinosis.

3. The method according to claim 1 or 2, wherein Y represents a $C_1$-$C_4$-alkoxy group;
  or an acid addition salt thereof, or an enantiomer or diastereoisomer thereof, or a mixture thereof.

4. The method according to claim 1 or 2, wherein Y represents an —NRR' group,
  or an acid addition salt thereof, or an enantiomer or diastereoisomer thereof, or a mixture thereof.

5. The method according to claim 1 or 2, wherein Y represents an —O(CH$_2$)$_n$—C(O)—NRR' group n is an integer equal to 1 or 2;
  or an acid addition salt thereof, or an enantiomer or diastereoisomer thereof, or a mixture thereof.

6. The method according to claim 1 or 2, where the compound is selected from the group consisting of:

(±)-2-amino-7-(3,4-dimethoxy-3-methylbut-1-yn-1-yl)-1-ethyl-N-methyl-4-oxo-1,4-dihydro-1,8-naphthyridine-3-carboxamide;

2-amino-7-[3-(2-amino-2-oxoethoxy)-3-methylbut-1-yn-1-yl]-1-ethyl-N-methyl-4-oxo-1,4-dihydro-1,8-naphthyridine-3-carboxamide; and 2-amino-1-ethyl-7-(3-methoxyprop-1-yn-1-yl)-N-methyl-4-oxo-1,4-dihydro-1,8-naphthyridine-3-carboxamide;

or an acid addition salt thereof.

7. The method according to claim 1 or 2 wherein $R_1$ and $R_2$ are hydrogen, $R_3$ is ethyl, $R_4$ is methyl and Y is

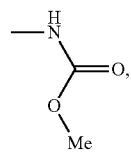

or an acid addition salt thereof.

8. The method according to claim 1 or 2 where $R_1$, $R_2$ and $R_4$ is methyl, $R_3$ is ethyl and Y is $NH_2$ or an acid addition salt thereof.

* * * * *